(12) United States Patent
Gregory et al.

(10) Patent No.: US 8,598,196 B2
(45) Date of Patent: Dec. 3, 2013

(54) METHODS OF TREATING DERMATOLOGICAL DISORDERS AND INDUCING INTERFERON BIOSYNTHESIS WITH SHORTER DURATIONS OF IMIQUIMOD THERAPY

(75) Inventors: Jefferson J. Gregory, Bristol, TN (US); Michael T. Nordsiek, Wayne, PA (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 0 days.

(21) Appl. No.: 13/552,543

(22) Filed: Jul. 18, 2012

(65) Prior Publication Data

US 2012/0283286 A1 Nov. 8, 2012

Related U.S. Application Data

(63) Continuation of application No. 12/543,434, filed on Aug. 18, 2009, now abandoned.

(60) Provisional application No. 61/090,132, filed on Aug. 19, 2008, provisional application No. 61/089,887, filed on Aug. 18, 2008.

(51) Int. Cl.
*A01N 43/42* (2006.01)
*A61K 31/44* (2006.01)
*C07D 235/02* (2006.01)

(52) U.S. Cl.
USPC ........................................ 514/293; 548/302.1

(58) Field of Classification Search
USPC ........................................ 514/293; 548/302.1
See application file for complete search history.

(56) References Cited

U.S. PATENT DOCUMENTS

| | | | |
|---|---|---|---|
| 4,411,893 A | 10/1983 | Johnson et al. |
| 4,689,338 A | 8/1987 | Gerster |
| 4,722,941 A | 2/1988 | Eckert et al. |
| 4,746,515 A | 5/1988 | Cheng et al. |
| 4,751,087 A | 6/1988 | Wick |
| 4,929,624 A | 5/1990 | Gerster et al. |
| 5,238,944 A | 8/1993 | Wick et al. |
| 5,346,905 A | 9/1994 | Gerster |
| 5,736,553 A | 4/1998 | Wick et al. |
| 6,245,776 B1 | 6/2001 | Skwierczynski et al. |
| 6,335,030 B1 | 1/2002 | Hoeck et al. |
| 6,486,168 B1 | 11/2002 | Skwierczynski et al. |
| 6,693,113 B2 | 2/2004 | Lindstrom |
| 6,706,728 B2 | 3/2004 | Hedenstrom et al. |
| 6,894,060 B2 | 5/2005 | Slade |
| 7,038,051 B2 | 5/2006 | Gerster et al. |
| 7,179,253 B2 | 2/2007 | Graham et al. |
| 7,507,703 B2 | 3/2009 | Woodward |
| 7,521,459 B2 | 4/2009 | Baumann et al. |
| 7,655,672 B2 | 2/2010 | Statham et al. |
| 7,696,159 B2 | 4/2010 | Owens et al. |
| 7,699,057 B2 | 4/2010 | Miller et al. |
| 7,893,083 B2 | 2/2011 | Mandrea |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,906,524 B2 | 3/2011 | Statham et al. |
| 7,906,525 B2 | 3/2011 | Statham et al. |
| 7,906,526 B2 | 3/2011 | Statham et al. |
| 7,906,527 B2 | 3/2011 | Statham et al. |
| 7,915,277 B2 | 3/2011 | Statham et al. |
| 7,923,429 B2 | 4/2011 | Miller et al. |
| 7,928,116 B2 | 4/2011 | Statham et al. |
| 7,928,117 B2 | 4/2011 | Statham et al. |
| 7,928,118 B2 | 4/2011 | Statham et al. |
| 7,932,429 B2 | 4/2011 | Ragaru et al. |
| 2002/0147210 A1 | 10/2002 | Smith |
| 2003/0007939 A1 | 1/2003 | Murad |
| 2003/0072814 A1 | 4/2003 | Maibach et al. |
| 2003/0199538 A1 | 10/2003 | Skwierczynski et al. |
| 2004/0087614 A1 | 5/2004 | Baumann et al. |
| 2004/0180919 A1 | 9/2004 | Miller et al. |
| 2004/0181130 A1 | 9/2004 | Miller et al. |
| 2004/0192585 A1 | 9/2004 | Owens et al. |
| 2004/0265351 A1 | 12/2004 | Miller et al. |

(Continued)

FOREIGN PATENT DOCUMENTS

| | | |
|---|---|---|
| CN | 1583175 A | 2/2005 |
| EP | 1889609 A2 | 2/2008 |

(Continued)

OTHER PUBLICATIONS

Dockrell et al. "Imiquimod and resiquimod as novel immunomodulators" Journal of Antimicrobial Chemotherapy, 2001, vol. 48, pp. 751-755.*

Buck et al., "Imiquimod 5% cream in the treatment of anogenital warts in female patients," Int'l J. of Gynecology & Obstetrics, 77:231-238, 2002.

Burack, "Fake doctor sentenced to prison for scamming, injecting patients," [online], Sep. 2011 [retrieved on Aug. 7, 2012], Retrieved from the Internet: <URL:http://www.sfexaminer.com/local/crime/2011/09/fake-doctor-sentenced-prison-scamming-injecting-patients>.

(Continued)

*Primary Examiner* — Kendra D Carter
(74) *Attorney, Agent, or Firm* — Kilpatrick Townsend & Stockton LLP

(57) ABSTRACT

Pharmaceutical formulations and methods for the topical and/or transdermal delivery of imiquimod, including creams, ointments and pressure-sensitive adhesive compositions to treat dermatological disorders, namely, viral infections, such as Type I or Type II Herpes simplex infections and genital and perianal warts, actinic keratosis and superficial basal cell carcinoma, and to induce interferon biosynthesis to achieve an antiviral effect, with shorter durations of therapy, than currently approved for imiquimod by the Food & Drug Administration ("FDA").

2 Claims, No Drawings

(56) References Cited

U.S. PATENT DOCUMENTS

| | | |
|---|---|---|
| 2005/0048072 A1 | 3/2005 | Kedl et al. |
| 2005/0165043 A1 | 7/2005 | Miller et al. |
| 2005/0232869 A1 | 10/2005 | Tamarkin et al. |
| 2006/0105028 A1 | 5/2006 | Zhang et al. |
| 2006/0105029 A1 | 5/2006 | Zhang et al. |
| 2006/0195067 A1 | 8/2006 | Wolter et al. |
| 2006/0216333 A1 | 9/2006 | Miller et al. |
| 2007/0049518 A1 | 3/2007 | Chandler et al. |
| 2007/0081962 A1 | 4/2007 | Munshi |
| 2007/0123558 A1 | 5/2007 | Statham et al. |
| 2007/0123559 A1 | 5/2007 | Statham et al. |
| 2007/0134273 A1 | 6/2007 | Romagne et al. |
| 2007/0166384 A1 | 7/2007 | Zarraga |
| 2007/0190124 A1 | 8/2007 | Zhang et al. |
| 2007/0196293 A1 | 8/2007 | Zhang et al. |
| 2007/0196323 A1 | 8/2007 | Zhang et al. |
| 2007/0196452 A1 | 8/2007 | Zhang et al. |
| 2007/0196453 A1 | 8/2007 | Zhang et al. |
| 2007/0196457 A1 | 8/2007 | Zhang et al. |
| 2007/0264317 A1 | 11/2007 | Yosha et al. |
| 2007/0280972 A1 | 12/2007 | Zhang et al. |
| 2008/0015271 A1 | 1/2008 | Abram et al. |
| 2008/0025929 A1 | 1/2008 | Burton et al. |
| 2008/0125375 A1 | 5/2008 | Yang et al. |
| 2008/0125485 A1 | 5/2008 | Cuevas Sanchez et al. |
| 2008/0145375 A1 | 6/2008 | Bembridge et al. |
| 2008/0161328 A1 | 7/2008 | Muller et al. |
| 2008/0187511 A1 | 8/2008 | Shurin et al. |
| 2008/0193487 A1 | 8/2008 | Schild et al. |
| 2008/0214615 A1 | 9/2008 | Muller et al. |
| 2008/0275077 A1 | 11/2008 | Skwierczynski et al. |
| 2008/0280943 A1 | 11/2008 | Slade et al. |
| 2009/0018155 A1 | 1/2009 | Gregory |
| 2009/0041680 A1 | 2/2009 | Tamarkin et al. |
| 2009/0093514 A1 | 4/2009 | Statham et al. |
| 2009/0130029 A1 | 5/2009 | Tamarkin et al. |
| 2009/0163532 A1 | 6/2009 | Perman et al. |
| 2009/0182004 A1 | 7/2009 | Winckle et al. |
| 2009/0202443 A1 | 8/2009 | Miller et al. |
| 2009/0232755 A1 | 9/2009 | Baumann |
| 2009/0246156 A1 | 10/2009 | Kunin |
| 2009/0281047 A1 | 11/2009 | Brown |
| 2009/0304812 A1 | 12/2009 | Staniforth et al. |
| 2010/0021394 A1 | 1/2010 | Yu |
| 2010/0056557 A1 | 3/2010 | Benninghoff et al. |
| 2010/0092401 A1 | 4/2010 | Vallejo et al. |
| 2010/0096287 A1 | 4/2010 | Stoesz et al. |
| 2010/0129439 A1 | 5/2010 | Alexis et al. |
| 2010/0150869 A1 | 6/2010 | Sredni et al. |
| 2010/0160368 A1 | 6/2010 | Gregory |
| 2010/0180902 A1 | 7/2010 | Miller et al. |
| 2010/0197722 A1 | 8/2010 | Owens et al. |
| 2010/0267678 A1 | 10/2010 | Zhang et al. |
| 2011/0021555 A1 | 1/2011 | Nordsiek et al. |
| 2011/0038900 A1 | 2/2011 | Chakrapani et al. |
| 2011/0045037 A1 | 2/2011 | Tamarkin et al. |
| 2011/0135604 A1 | 6/2011 | Casarez et al. |
| 2011/0257216 A1 | 10/2011 | Nordsiek et al. |
| 2011/0257217 A1 | 10/2011 | Nordsiek et al. |
| 2011/0257218 A1 | 10/2011 | Nordsiek et al. |
| 2011/0263633 A1 | 10/2011 | Nordsiek et al. |
| 2011/0263634 A1 | 10/2011 | Nordsiek et al. |
| 2011/0263635 A1 | 10/2011 | Nordsiek et al. |
| 2011/0263636 A1 | 10/2011 | Nordsiek et al. |
| 2011/0263637 A1 | 10/2011 | Nordsiek et al. |

FOREIGN PATENT DOCUMENTS

| | | |
|---|---|---|
| EP | 1891953 | 2/2008 |
| IN | 1581/MUM/2005 | 8/2007 |
| WO | WO 00/40228 A1 | 7/2000 |
| WO | WO 02/102377 A1 | 12/2002 |
| WO | WO 03/045391 A1 | 6/2003 |
| WO | WO 2007/007208 A2 | 1/2007 |
| WO | WO 2007/044639 A2 | 4/2007 |
| WO | WO 2007/070643 A2 | 6/2007 |
| WO | WO 2007/070694 A2 | 6/2007 |
| WO | WO 2007/070695 A2 | 6/2007 |
| WO | WO 2008/010963 A2 | 1/2008 |
| WO | WO 2008/016475 A2 | 2/2008 |
| WO | WO 2008/098232 A1 | 8/2008 |
| WO | WO 2008/118762 A1 | 10/2008 |
| WO | WO 2008/118763 A1 | 10/2008 |
| WO | WO 2008/118765 A1 | 10/2008 |
| WO | WO 2008/140713 A1 | 11/2008 |
| WO | WO 2009/019473 A1 | 2/2009 |
| WO | WO 2009/091541 A1 | 7/2009 |
| WO | WO 2009/095226 A2 | 8/2009 |
| WO | WO 2009/155070 A2 | 12/2009 |
| WO | WO 2009/158687 A1 | 12/2009 |
| WO | WO 2010/050889 A1 | 5/2010 |
| WO | WO 2010/088924 A1 | 8/2010 |

OTHER PUBLICATIONS

Eron et al., "Interferon Therapy for Condylomata Acuminata," The New England J. of Med., 35(17):1059-1064, Oct. 23, 1986.

Garland et al., "Imiquimod 5% cream is a safe and effective self-applied treatment for anogenital warts—results of an open-label, multicentre Phase IIIB trial," Int'l J. of STD & AIDS, 12:722-729, 2001.

Stanley et al., "Immune responses to human papilloma viruses," Indian J. Med. Res., 130:266-276, 2009.

Syrjanen, "Annual disease burden due to human pappillomaviruse (HPV) 6 and 11 infections in Finland," Scandinavian J. of Infectious Diseases, Suppl. 107:3-32, 2009.

Vance et al., "Intralesional Recombinant Alpha-2 Interferon for the Treatment of Patients with Condyloma Acuminatum or Verruca Plantaris," Arch. Dermatol., 122:272-277, 1986.

Van Derbeken, "Fake doctor fleeced patients, prosecutors say," [online], Feb. 2010 [retreived on Aug. 7, 2012], Retrieved from the Internet: <URL:http://www.sfgate.com/default/article/Fake-doctor-fleeced-patients-prosecutors-say-3201225.php>.

Aldara Package Insert, obtained Sep. 3, 2002 online at http://www.accessdata.fda.gov/drugsaUda docs/label/2002/20723s11 s121bl.pdf.

Alomar, A. et al., "Vehicle-controlled, randomized, double-blind study to assess safety and efficacy of imiquimod 5% cream applied once daily 3 days per week in one or two courses of treatment of actinic keratoses on the head," Br. J. Dermatol., 157(1):133-41, 2007.

Arican et al., "Topical Imiquimod 5% Cream in External Anogential Warts: A Randomized, Double-Blind, Placebo-Controlled Study," The Journal of Dermatology, 2004, vol. 31: 627-631.

Ben M'Barek, L. et al., "5% topical imiquimod tolerance in transplant recipients," Dermatol., 215(2):130-3, 2007.

Berman, B. "Imiquimod: a new immune response modifier for the treatment of external genital warts and other diseases in dermatology," Int. J. Dermatol., 41(Suppl S1):7-11, 2002.

Berman, B. et al., "Determination of the area of skin capable of being covered by the application of 250 mg of 5% imiquimod cream," Dermatologic surgery: Official Publication for American Society for Dermatologic Surgery, 30(5):784-786, 2004.

Berman, B. et al., "Novel dermatologic uses of the immune response modifier imiquimod 5% cream," Skin Therapy Lett., 7(9):1-6, 2002.

Berman, B. et al., "Pharmacotherapy of actinic keratosis," Expert Opin. Pharmacother., 10(18):3015-31, 2009.

Beutner, K. et al., "Imiquimod, a patient-applied immune-response modifier for treatment of external genital warts," Antimicrobial Agents and Therapy, 42:789-794, 1998.

Beutner, K. et al., "Treatment of genital warts with an immune-response modifier (imiquimod)," J. Am. Acad. Dermatol., 1998, 38(2 Pt 1):230-9.

Bianchi, L. et al., "Actinic keratasis treated with an immune response modifier: a case report of six patients," Clin. Exp. Dermatol., 28(Suppl 1):39-41, 2003.

Bukhardt Pérez, M. et al., "Basal cell carcinoma: treatment with imiquimod," Int. J. Derm., 46:539-542, 2007.

Burns, C., "Imiquimod for the treatment of skin cancer," Dermatol. Clin., 23(1):151-64, 2005.

(56) References Cited

OTHER PUBLICATIONS

Chen, J. et al., "Short-course therapy with imiquimod 5% cream for solar keratoses: A randomizedcontrolled trial," Australasian J. Dermatol., 44:250-255, 2003.
Chollet, J. et al., "Development of a topically active imiquimod formulation," Pharm. Devel. Tech., 4(1):35-43, 1999.
Del Rosso, J. et al., "Safety and efficacy of multiple 16-week courses of topical imiquimod for the treatment of large areas of skin involved with actinic keratoses," J. Clin. Aesth. Dermatol., 2(4):20-8, 2009.
Del Rosso, J., "New and emerging topical approaches for actinic keratoses," Cutis., 72(4):273-6, 279, 2003.
Del Rosso, J., "The use of topical imiquimod for the treatment of actinic keratosis: a status report," Cutis, 76(4):241-8, 2005.
Edwards et al., "Self-administered topical 5% imiquimod cream for external anogenital warts," Arch. Dermatol., 134:25-30, 1998.
Edwards et al., "Effect of intralesional alpha-2 interferon on actinic keratosis," Arch. Dermatol., 122:779-782, 1986.
Edwards, L. et al., "Imiquimod in clinical practice," Arch. Derm., 42:789-94, 1998. (Also reported in Aus. J. Derm., 39:S14-S16, 1998.).
Ezughah, F. et al., "Confirmation of histological clearance of superficial basal cell carcinoma with multiple serial sectioning and Mohs' micrographic surgery following treatment with imiquimod 5% cream," J. Derm. Treat., 19:111-117, 2008.
Fife, K. et al., "Treatment of External Genital Warts in Men Using 5% Imiquimod Cream Applied Three Times a Week, Once Daily, Twice Daily, or Three Times a Day," Sexually Transmitted Diseases, 2001 28(4):226-31.
Final Office Action dated Jan. 19, 2011 in U.S. Appl. No. 12/028,771.
Garland, S., "An open-label phase II pilot study investigating the optimal duration of imiquimod 5% cream for the treatment of external genital warts in women," Int. J. STD & AIDS, 2006,17(7):448-52.
Garland, S., "Imiquimod," Curr. Opin. Infect. Dis., 16(2):85-9, 2003.
Gebauer, K. et al., "Effect of dosing frequency on the safety and efficacy of imiquimod 5% cream for treatment of actinic keratosis on the forearms and hands: a phase II, randomized placebo-controlled trial," Br. J. Dermatol., 161(4):897-903, 2009.
Gollnick, H. et al., "Safety and efficacy of imiquimod 5% cream in the treatment of penile genital warts in uncircumcised men when applied three times weekly or once per day," Int. J. STD & AIDS, 2001, 12(1):22-8.
Gotovtseva, E. et al., "Optimal frequency of imiquimod (Aldara) 5% cream for the treatment of external genital warts in immunocompetent adults: a meta-analysis," Sexually Transmitted Diseases, 35(4):346-351, 2008.
Gupta, A. et al., "Imiquimod: a review," J. Cutan. Med. Surg., 6(6):554-60, 2002.
Gupta, A. et al., "Viral and nonviral uses of imiquimod: a review," J. Cutaneous Med. Surg., 8(5):338-52, 2004.
Gupta, A. et al., "Evaluation of the effectiveness of imiquimod and 5-fluorouracil for the treatment of actinic keratosis: Critical review and meta-analysis of efficacy studies," J. Cutan. Med. Surg., 9(5):209-14, 2005.
Hadley, G. et al., "Imiquimod for actinic keratosis: systematic review and meta-analysis," J. Invest. Dermatol., 126(6):1251-5, 2006.
Harrison, L. et al., "Pharmacokinetics and safety of imiquimod 5% cream in the treatment of actinic kertoses of the face, scalp, or hands and arms," Arch. Dermatol. Res., 296:6-11, 2004.
Harrison, L. et al., "A pharmaceutical comparison of different commercially available imiquimod 5% cream poducts," J. Dermatol. Treat., 20(3):160-164, 2009.
He, Q., "Preparation of imiquimod cream and its clinical application in the treatment of condyloma acuminatum," Herald of Medicine, Yiyao Daobao, 23(10):758-760, 2004. (English abstract).
International Search Report and Written Opinion dated Jun. 27, 2008 in PCT/US0853522.
Jorizzo, J. et al., "Vehicle-controlled, double-blind, randomized study of imiquimod 5% cream applied 3 days per week in one or two courses of treatment for actinic keratoses on the head," J. Am. Acad. Dermatol., 57(2):265-8, 2007.
Korman, N. et al., "Dosing with 5% imiquimod cream 3 times per week for the treatment of actinic keratosis: results of two phase 3, randomized, double-blind, parallel-group, vehicle-controlled trials," Arch. Dermatol. Res., 141(4):467-73, 2005.
Kose, O. et al., "Comparison of the efficacy and tolerability of 3% diclofenac sodium gel and 5% imiquimod cream in the treatment of actinic keratosis," J. Dermatol. Treat., 19(3):159-63, 2008.
Krawtchenko, N., "A randomised study of topical 5% imiquimod vs. topical5-fluorouracil vs. cryosurgery in immunocompetent atients with actinic keratoses: a comparison of clinical and histological outcomes including 1-year follow-up," Br. J. Dermatol., 157(Suppl. 2):34-40, 2007.
Lebwohl, M. et al., "Imiquimod 5% cream for the treatment of actinic keratosis: results from two phase III, randomized, double-blind, parallel group, vehicle-controlled trials," J. Am. Acad. Dermatol., 50(5):714-21, 2004.
Love, W. et al., "Topical Imiquimod or Fluorouracil Therapy for Basal and Squamous Cell Carcinoma," Arch. Derm., 145:1431-1438, 2009.
Majewski, S. et al., "Imiquimod is a strong inhibitor of tumor cell-induced angiogenesis," Int. J. Dermatol., 44(1):14-19, 2005.
Miller, R. et al., "Review article imiquimod applied topically: a novel immune response modifier and new class of drug," Int. J. of Immunopharm., 21(1):1-14, 1999.
Monograph of Aldara Product (Feb. 3, 2004).
Muzio, G. et al., "Treatment of non-genital warts with topical imiquimod 5% Cream," Eur. J. Derm., 12:347-349, 2002.
Non-final Office Action dated May 4, 2010 in U.S. Appl. No. 12/028,771.
Ooi, T. et al., "Imiquimod-induced regression of actinic keratosis is associated with infiltration by Tlymphocytes and dendritic cells: a randomized controlled trial," Br. J. Dermatol., 154(1):72-8, 2006.
Papadavid, E. et al., "Imiquimod: an immune response modifier in the treatment of precancerous skin lesions and skin cancer," Expert Opin. Pharmacother., 8(11):1743-55, 2007.
Perras, C., "Imiquimod 5% cream for actinic keratosis," Issues Emerg. Health Technol., 61:1-4, 2004.
Persaud, A. et al., "Clinical effect of imiquimod 5% cream in the treatment of actinic keratosis," J. Am. Acad. Dermatol., 47(4):553-6, 2002.
Persaud, A. et al., "Imiquimod cream in the treatment of actinic keratoses," J. Am. Acad. Dermatol., 47(4 Suppl): S236-9, 2002.
Peters-Kennedy, J. et al., "Apparent clinical resolution of pinnal actinic keratoses and squamous cell carcinoma in a cat using topical imiquimod 5% cream," J Feline Med. Surg., 10(6):593-9, 2008.
Quirk, C. et al., "Two-year interim results from a 5-year study evaluating clinical recurrence of superficial basal cell carcinoma after treatment with imiquimod 5% cream daily for 6 weeks," Aus. J. Derm., 47:258-265, 2006.
Ramoni, S. et al., "Penile intraepithelial carcinoma treated with imiquimod 1% in an HIV-positive patient," J. Derm. Treatment, 20: 177-178, 2009.
Rivers, J. et al., "Open-label study to assess the safety and efficacy of imiquimod 5% cream applied once daily three times per week in cycles for treatment of actinic keratoses on the head," J. Cutaneous Med. Surgery, 12(3):97-101, 2008.
Salasche, S. et al., "Cycle therapy of actinic keratoses of the face and scalp with 5% topical imiquimod cream: An open-label trial," J. Am. Acad. Dermatol., 47(4):571-7, 2002.
Schulze, H. et al., "Imiquimod 5% cream for the treatment of superficial basal cell carcinoma: results from a randomized vehicle-controlled phase III study in Europe," British J. Derm., 152:939-947, 2005.
Shaffelburg, M., "Treatment of actinic keratoses with sequential use of photodynamic therapy; and imiquimod 5% cream," J. Drugs Dermatol., 8(1):35-39, 2009.
Skinner, R., "Role of topical therapies in the management of cutaneous disease," J. Cutan. Med. Surg., 8(Suppl 3):22-31, 2004.
Somani, N. et al., "Imiquimod 5% cream for the treatment of actinic keratoses," Skin Ther. Lett., 10(2):1-6, 2005.
Sotiriou, E. et al., "Intraindividual, right-left comparison of topical 5-aminolevulinic acid photodynamic therapy vs. 5% imiquimod

(56) References Cited

OTHER PUBLICATIONS cream for actinic keratoses on the upper extremities," J. Eur. Acad. Dermatol. Venereol., 23(9):1061-5, 2009.

Stockfleth, E. et al., "A randomized, double-blind, vehicle-controlled study to assess 5% imiquimod cream for the treatment of multiple actinic keratoses," Arch. Dermatol., 138(11):1498-502, 2002.

Stockfleth, E. et al., "Multicentre, open-label study using imiquimod 5% cream in one or two 4-week courses of treatment for multiple actinic keratoses on the head," Br. J. Dermatol., 157(Suppl 2):41-6, 2007.

Stockfleth, E. et al., "Treatment of multiple, multiform actinic keratoses on the head with imiquimod 5% cream," Eur. J. Dermatol., 19(4):355-9, 2009.

Stockfleth, E. et al., "Successful treatment of actinic keratosis with imiquimod cream 5%: a report of six cases," Br. J. Dermatol., 144(5):1050-3, 2001.

Stockfleth, E., "Topical management of actinic keratosis and field cancerisation," G. Ital. Dermatol. Venereol., 144(4):459-62, 2009.

Swanson, N. et al., "Optimizing imiquimod for actinic keratoses on face or scalp: imiquimod 2.5% and 3.75% daily for two 2-week or 3-week cycles," The 12th World Congress on Cancers of the Skin, Presentation Date: May 4, 2009.

Syed et al., "Treatment of genital herpes in males with imiquimod 1% cream a randomised, double-blind, placebo-controlled study," Clin. Drug Invest., 16:187-191, 1998.

Syed, T. et al., "Management of female genital warts with an analog of imiquimod 2% in cream: a randomized, double-blind, placebo-controlled study," J. Dermatol., 25:429-33, 1998.

Syed, T. et al., "Treatment of external genital warts in men with imiquimod 2% in cream. A placebo-controlled, double-blind study," J. Infection, 41:148-151, 2000.

Szeimies, R. et al., "Imiquimod 5% cream for the treatment of actinic keratosis: results from a phase III, randomized, double-blind, vehicle-controlled, clinical trial with histology," J. Am. Acad. Dermatol., 51(4):547-55, 2004.

Tan, J. et al., "Efficacy of imiquimod as an adjunct to cryotherapy for actinic keratoses," J. Cutan. Med. Surg., 11(6):195-201, 2007.

Tanghetti, E. et al., "Comparison of 5% 5-fluorouracil cream and 5% imiquimod cream in the management of actinic keratoses on the face and scalp," J. Drugs Dermatol., 6(2):144-7, 2007.

Trofatter, K. et al., "Increased frequency of dosing of imiquimod 5% cream in the treatment of external genital warts in women," Int. J. Gynecol. Obstet., 2002, 76(2):191-3.

Torres, A. et al., "Immune-mediated changes in actinic keratosis following topical treatment with imiquimod 5% cream," J. Transl. Med., 5(7):1-18, 2007.

Travis, L. et al., "Successful treatment of vulvar intraepitheilial neoplasia with topical imiquimod 5% cream in a lung transplanted patient," Acta Derm. Venereol., 82:475-6, 2002.

Tyring, S., "Imiquimod applied topically: A novel immune response modifier," Skin Therapy Lett., 6(6)1-4, 2001.

Tyring, S. et al., "A randomized, controlled, molecular study of condylomata acuminata clearance during treatment with imiquimod," J. Infect. Dis., 1998, 178(2):551-5.

Ulrich, C. et al., "Topical immunomodulation under systemic immunosuppression: results of a multicentre, randomized, placebo-controlled safety and efficacy study of imiquimod 5% cream for the treatment of actinic keratoses in kidney, heart, and liver transplant patients," Br. J. Dermatol., 157(Suppl 2):25-31, 2007.

Vidal, D., "Topical imiquimod: mechanism of action and clinical applications," Mini Rev. Med. Chem., 6(5):499-503, 2006.

Wagstaff, A. et al., "Topical imiquimod: a review of its use in the management of anogenital warts, actinic keratoses, basal cell carcinoma and other skin lesions," Drugs, 67(15):2187-210, 2007.

Wagman, F. et al., "Self-Administered Topical 5% Imiquimod Cream for External Anogenital Warts in Adolescent Girls," Obset. Gynecol., 2001, 97:S14.

Walker, J. et al., "Is imiquimod effective and safe for actinic keratosis?," J. Fam. Pract., 52(3):84-5, 2003.

Wu, J. et al., "Treatment of Bowen's disease and basal cell carcinoma of the nose with imiquimod 5% cream," Australasian J. Dermatol., 44(2):123-125, 2003.

Zeichner, J. et al., "Placebo-controlled, double-blind, randomized pilot study of imiquimod 5% cream applied once per week for 6 months for the treatment of actinic keratoses," J. Am. Acad. Dermatol., 60(1):59-62, 2009.

Drug Therapy in Nursing, Third Edition, 2009, by Aschenbrenner et al., Wolters Kluwer Health, Lippincott Williams & Wilkins, Philadelphia, PA, p. 51.

Office Action mailed Feb. 26, 2013 for U.S. Appl. No. 13/559,473, filed Jul. 26, 2012; First Named Inventor: Michael T. Nordsiek: Confirmation No. 5746; 25 pages.

Kim, Se-Jeong et al., "Analysis of cellular and behavioral responses to imiquimod reveals a unique itch pathway in transient receptor potential vanilloid 1 (TRPV1)—expressing neurons," PNAS, Feb. 22, 2011, vol. 108, No. 8, pp. 3371-3376.

* cited by examiner

METHODS OF TREATING DERMATOLOGICAL DISORDERS AND INDUCING INTERFERON BIOSYNTHESIS WITH SHORTER DURATIONS OF IMIQUIMOD THERAPY

FIELD OF THE INVENTION

This invention pertains to methods and pharmaceutical formulations for the topical or transdermal delivery of 1-isobutyl-1H-imidazo[4,5-c]-quinolin-4-amine, i.e., imiquimod. More particularly, it pertains to creams, ointments, foams, gels, lotions, pressure sensitive adhesive coatings and adhesive-coated sheet materials, which contain low dose imiquimod, that enhance skin penetration of drugs to treat dermatological disorders, namely, viral infections, such as Type I or Type II Herpes simplex infections and external genital and perianal warts, actinic keratosis and superficial basal cell carcinoma, and to induce interferon biosynthesis, to achieve an antiviral effect, with shorter durations of therapy, than currently approved for imiquimod by the Food & Drug Administration ("FDA").

BACKGROUND

The compound 1-isobutyl-1H-imidazo[4,5-c]-quinolin-4-amine, known as imiquimod and commercially marketed in the U.S. under the brand name Aldara®, is disclosed in U.S. Pat. No. 4,689,338 and described therein as an antiviral agent and as an interferon inducer, which is incorporated herein by reference in its entirety. A variety of formulations for topical administration of imiquimod are also described therein. This U.S. Pat. No. 4,689,338 is incorporated herein by reference in its entirety U.S. Pat. No. 4,751,087 discloses the use of a combination of ethyl oleate and glyceryl monolaurate as a skin penetration enhancer for nitroglycerine, with all three components being contained in the adhesive layer of a transdermal patch, wherein this U.S. patent is incorporated herein by reference in its entirety.

U.S. Pat. No. 4,411,893 discloses the use of N,N-dimethyldodecylamine-Noxide as a skin penetration enhancer in aqueous systems, wherein this U.S. patent is incorporated herein by reference in its entirety.

U.S. Pat. No. 4,722,941 discloses readily absorbable pharmaceutical compositions that comprise a pharmacologically active agent distributed in a vehicle comprising an absorption-enhancing amount of at least one fatty acid containing 6 to 12 carbon atoms and optionally a fatty acid monoglyceride. Such compositions are said to be particularly useful for increasing the absorption of pharmacologically active bases, wherein this U.S. patent is incorporated herein by reference in its entirety.

U.S. Pat. No. 4,746,515 discloses a method of using glyceryl monolaurate to enhance the transdermal flux of a transdermally deliverable drug through intact skin, wherein this U.S. patent is incorporated herein by reference in its entirety.

U.S. Pat. No. 5,238,944 discloses topical formulations and transdermal delivery systems containing 1-isobutyl-1H-imidazo[4,5-c]quinolin-4-amine, wherein this U.S. patent is incorporated herein by reference in its entirety.

SUMMARY OF THE INVENTION

The present invention provides a substantially non-irritating pharmaceutical formulation for topical and/or transdermal administration of the imiquimod, which formulation comprises:

a) 1-isobutyl-1H-imidazo[4,5-c]-quinolin-4-amine, i.e., imiquimod, in an amount of about 2 percent to about 4 percent by weight based on the total weight of the formulation; and b) a pharmaceutically acceptable vehicle for imiquimod, which vehicle comprises a fatty acid, such as isostearic acid, linoleic acid, oleic acid, super purified oleic acid (an oleic acid having low polar impurities such as peroxides) and a combination thereof, in a total amount of about 3 percent to about 45 percent by weight based on the total weight of the formulation. The formulation is further characterized in that when tested in the hairless mouse skin model described in U.S. Pat. No. 5,238,944, the formulation provides a penetration of the agent of at least about 10% (and preferably at least about 15%) of the total amount of the agent contained in the formulation in 24 hours.

The salient elements of a pharmaceutical formulation according to the invention are (a) imiquimod and (b) a fatty acid, e.g., isostearic, linoleic, super purified oleic or oleic acid and mixtures thereof. A pharmaceutical formulation of the invention can be in any form known to the art, such as a cream, an ointment, a foam, a gel, a lotion or a pressure-sensitive adhesive composition, each form containing the necessary elements in particular amounts and further containing various additional elements.

A cream of the invention preferably contains about 2 percent to about 4 percent by weight of imiquimod based on the total weight of the cream; about 5 percent to about 25 percent by weight of fatty acid, based on the total weight of the cream; and optional ingredients such as emollients, emulsifiers, thickeners, and/or preservatives.

An ointment of the invention contains an ointment base in addition to imiquimod and fatty acid. An ointment of the invention preferably contains about 2 percent to about 4 percent by weight imiquimod; about 3 percent to about 45 percent, more preferably about 3 percent to about 25 percent by weight fatty acid; and about 40 percent to about 95 percent by weight ointment base, all weights being based on the total weight of the ointment. Optionally, an ointment of the invention can also contain emulsifiers, emollients and thickeners.

A pressure-sensitive adhesive composition of the invention contains imiquimod, fatty acid, and an adhesive. The adhesives utilized in a pressure sensitive adhesive composition of the invention are preferably substantially chemically inert to imiquimod. A pressure sensitive adhesive composition of the invention preferably contains about 2 percent to about 4 percent by weight imiquimod; about 10 percent to about 40 percent by weight, more preferably of about 15 percent to about 30 percent by weight, and most preferably about 20 percent to about 30 percent by weight of fatty acid; all weights being based on the total weight of the pressure sensitive adhesive composition.

Optionally, pressure sensitive adhesive compositions of the invention can also contain one or more skin penetration enhancers. The total amount of skin penetration enhancer(s) present in a pressure sensitive adhesive composition of the invention is preferably about 3 percent to about 25 percent by weight, and more preferably about 3 percent to about 10 percent by weight based on the total weight of the pressure sensitive adhesive composition.

A pressure sensitive adhesive coated sheet material of the invention can be made from a pressure-sensitive adhesive composition of the invention in the form of an article such as a tape, a patch, a sheet, or a dressing.

A formulation of the present invention may be used to topically and/or transdermally administer imiquimod for effectively treating viral infections, for example, Type I or Type II Herpes simplex infections, actinic keratosis and superficial basal cell carcinoma for a shorter duration of time and with the same or increased number of applications per week, as compared to current imiquimod topical therapy.

For example, a formulation of the present invention containing between greater than about 1% and about 5% imiquimod may be applied from three to seven times per week (once per day) for 8 to 12 weeks to treat viral infections, for example, Type I or Type II Herpes simplex infections, actinic keratosis and superficial basal cell carcinoma or to induce interferon biosynthesis. It should be understood that while formulations of the present invention containing between greater than about 1% and about 5% imiquimod are preferred, formulations containing about 2.0%, 2.25%, 2.5%, 2.75%, 3.0%, 3.25%, 3.5%, 3.75%, 4.0%, 4.25% and 4.5% are more preferred and that formulations containing about 2.5%, 2.75%, 3.0%, 3.25%, 3.5%, 3.75% and 4.0% are most preferred.

As to duration, the present invention contemplates applying an effective amount of imiquimod for a shorter period of time than currently approved by the FDA. More specifically, the present invention contemplates applying an effective amount of imiquimod from three to seven times or more per week to an area in need of imiquimod treatment for about 8 to about 12 weeks, and more preferably between about 4, about 5, about 6 and about 7 times a week for about 8, about 9 or about 10 weeks. More preferably, examples of shorter periods of treatment with low dose imiquimod for treating actinic keratosis and warts, e.g., external genital and perianal, as contemplated by the present invention comprise:

(a) applying an effective imiquimod dose of the lose dose imiquimod formulations, such as about 2.0%, 2.25%, 2.5%, 2.75%, 3.0%, 3.25%, 3.5%, 3.75%, 4.0%, 4.25% or 4.5% imiquimod % w/w, to the area affected with actinic keratosis, as follows: applying an effective amount once per day for fourteen (14) consecutive days, followed by no application for fourteen (14) days, followed by again applying an effective amount once per day for fourteen (14) days for a total of twenty-eight (28) doses to treat actinic keratosis;

(b) applying an effective imiquimod dose of the lose dose imiquimod formulations, such as about 2.0%, 2.25%, 2.5%, 2.75%, 3.0%, 3.25%, 3.5%, 3.75%, 4.0%, 4.25% or 4.5% imiquimod % w/w, to the area affected with actinic keratosis, as follows: applying an effective amount once per day for twenty one (21) days, followed by no application for twenty one (21) days, followed by again applying an effective amount once per day for twenty one (21) consecutive days for a total of forty-two (42) doses to treat actinic keratosis;

(c) applying an effective imiquimod dose of the lose dose imiquimod formulations to the warts, such as about 2.0%, 2.25%, 2.5%, 2.75%, 3.0%, 3.25%, 3.5%, 3.75%, 4.0%, 4.25% or 4.5% imiquimod % w/w, once per day, each day, for up to 56 consecutive days or 8 consecutive weeks or until clearance is observed, which ever occurs earlier to treat the warts; or (d) applying an effective imiquimod dose of a lose dose imiquimod formulation, such as about 2.0%, 2.25%, 2.5%, 2.75%, 3.0%, 3.25%, 3.5%, 3.75%, 4.0%, 4.25% or 4.5% imiquimod % w/w, to a dermatological area, once per day, each day, for:

(i) up to about 56 consecutive days or about 8 consecutive weeks to induce effective interferon biosynthesis;

(ii) fourteen (14) days, followed by no application for fourteen (14) days, followed by again applying an effective amount imiquimod dose once per day for fourteen (14) consecutive days for a total of twenty-eight (28) doses to induce effective interferon biosynthesis; or (iii) twenty one (21) days, followed by no application for twenty one (21) days, followed by again applying an effective imiquimod dose once per day for twenty one (21) consecutive days for a total of forty-two (42) doses to induce effective interferon biosynthesis.

While the present invention has identified what it believes to be preferred concentrations of imiquimod, numbers of applications per week and durations of therapy, it should be understood by those versed in this art that any effective concentration of imiquimod in a formulation and any numbers of application per week that can accomplish a reduction in therapy duration to effectively treat Type I or Type II Herpes simplex infections, actinic keratosis and superficial basal cell carcinoma or induce effective interferon biosynthesis is contemplated by the present invention.

DETAILED DESCRIPTION OF THE INVENTION

As used in the specification and claims, the phrase "substantially non-irritating" designates formulations that do not cause unacceptable skin irritation in conventional repeat skin irritation tests in albino rabbits such as that described in Draize et al, "Appraisal of the Safety of Chemicals in Food, Drugs and Cosmetics", prepared by the Division of Pharmacology of the Food and Drug Administration, published originally in 1959 by the Association of Food and Drug Officials of the United States, Topeka, Kans. (2nd printing 1965), incorporated herein by reference.

The present invention provides pharmaceutical formulations such as creams, ointments, foams, gels, lotions and adhesive coatings that contain imiquimod and a fatty acid such as isostearic, linoleic, super purified oleic acid or oleic acid and mixtures thereof. The formulations of the invention provide desirable skin penetrability of the imiquimod.

The compound imiquimod is a known antiviral agent that is also known to induce interferon biosynthesis. It can be prepared using the method disclosed in U.S. Pat. No. 4,689,338, the disclosure of which is incorporated herein by reference. The compound can be used to treat viral infections such as Type I or Type II Herpes simplex infections and genital warts. Furthermore, the fact that the compound is an interferon inducer suggests that it, and therefore formulations containing it, might be useful in the treatment of numerous other diseases, such as rheumatoid arthritis, warts, eczema, hepatitis B, psoriasis, multiple sclerosis, essential thrombocythemia, and cancer, such as basal cell carcinoma and other neoplastic diseases. The amount of imiquimod present in a formulation of the invention will be an amount effective to treat the targeted disease state to prevent the recurrence of such a disease or to promote immunity against such a disease. The amount is preferably about 0.5 percent to about 9 percent by weight based on the total weight of a formulation, more preferably between greater than about 1% and about 5% imiquimod, and more preferably between about 2.0%, 225%, 2.5%, 2.75%, 3.0%, 3.25%, 3.5%, 3.75%, 4.0%, 4.25% and 4.5%, and most preferred between about 2.75%, 3.0%, 3.25%, 3.5%, 3.75% and 4.0%. Likewise, the shortened period or duration, as contemplated by the present invention, will be for reduced periods of time effective to treat the targeted disease as discussed herein above. By way of example, shorter periods of treatment with low dose imiquimod for treating actinic keratosis and warts, e.g., external genital and perianal, or inducing interferon biosynthesis to achieve an effective antiviral effect, include:

(a) applying an effective imiquimod dose of the lose dose imiquimod formulations, such as about 2.0%, 2.25%, 2.5%, 2.75%, 3.0%, 3.25%, 3.5%, 3.75%, 4.0%, 4.25% or 4.5% imiquimod % w/w, to the area affected with actinic keratosis, as follows: applying an effective amount once per day for fourteen (14) consecutive days, followed by no application for fourteen (14) days, followed by again applying an effective amount once per day for fourteen (14) days for a total of twenty-eight (28) doses to treat actinic keratosis;

(b) applying an effective imiquimod dose of the lose dose imiquimod formulations, such as about 2.0%, 2.25%, 2.5%, 2.75%, 3.0%, 3.25%, 3.5%, 3.75%, 4.0%, 4.25% or 4.5% imiquimod % w/w, to the area affected with actinic keratosis, as follows: applying an effective amount once per day for twenty one (21) days, followed by no application for twenty one (21) days, followed by again applying an effective amount once per day for twenty one (21) consecutive days for a total of forty-two (42) doses to treat actinic keratosis;

(c) applying an effective imiquimod dose of the lose dose imiquimod formulations to the warts, such as about 2.0%, 2.25%, 2.5%, 2.75%, 3.0%, 3.25%, 3.5%, 3.75%, 4.0%, 4.25% or 4.5% imiquimod % w/w, once per day, each day, for up to 56 consecutive days or 8 consecutive weeks or until clearance is observed, which ever occurs earlier to treat the warts; or (d) applying an effective imiquimod dose of a lose dose imiquimod formulation, such as about 2.0%, 2.25%, 2.5%, 2.75%, 3.0%, 3.25%, 3.5%, 3.75%, 4.0%, 4.25% or 4.5% imiquimod % w/w, to a dermatological area, once per day, each day, for:

(i) up to about 56 consecutive days or about 8 consecutive weeks to induce effective interferon biosynthesis and an antiviral effect;

(ii) fourteen (14) days, followed by no application for fourteen (14) days, followed by again applying an effective amount imiquimod to a mammal dose once per day for fourteen (14) consecutive days for a total of twenty-eight (28) doses to induce effective interferon biosynthesis and an antiviral effect; or (iii) twenty one (21) days, followed by no application for twenty one (21) days; followed by again applying an effective imiquimod dose once per day for twenty one (21) consecutive days for a total of forty-two (42) doses to induce effective interferon biosynthesis and an antiviral effect.

A fatty acid such as isostearic acid, linoleic acid, refined or super purified oleic acid, unrefined oleic acid blended with effective amounts of antioxidants or mixtures thereof are incorporated into formulations of the present invention. The total amount of fatty acid present in a formulation is preferably between about 3 percent and about 45 percent by weight based on the total weight of a formulation. It should be understood that when oleic acid is selected as a fatty acid, that stability may present issue. Thus, stabilizers, such as antioxidants and the like, may be required to preserve pharmaceutical elegance and stability over the life of the oleic acid formulation.

A pharmaceutical formulation of the invention can be in a form such as a cream, an ointment, a foam, a gel, a lotion, a pressure-sensitive adhesive composition, or other forms known to those skilled in the art, each particular form containing imiquimod and fatty acid in particular amounts, and optionally containing various additional elements. The preferred amounts of drug and fatty acid, and the amounts and types of optional elements used in formulations of the invention are discussed below with particular reference to creams, ointments and adhesive compositions.

A cream according to the invention contains 1-isobutyl-1H-imidazo[4,5-c]quinolin-4-amine and fatty acid.

The amount of 1-isobutyl-1H-imidazo[4,5-c]-quinolin-4-amine present in a cream is preferably about 0.5 percent to about 9 percent by weight, and more preferably about 1 percent to about 5 percent by weight, based on the total weight of the cream.

The total amount of fatty acid present in a cream of the invention is preferably about 3 percent to about 45 percent by weight, and more preferably about 5 percent to about 25 percent by weight, based on the total weight of the cream.

Optionally, a cream of the present invention can contain emollients, emulsifiers, thickeners, and/or preservatives.

Emollients such as long chain alcohols, e.g., cetyl alcohol, stearyl alcohol and cetearyl alcohol; hydrocarbons such as petrolatum and light mineral oil; or acetylated lanolin can be included in a cream of the invention. A cream can contain one or more of these emollients. The total amount of emollient in a cream of the invention is preferably about 5 percent to about 30 percent, and more preferably about 5 percent to about 10 percent by weight based on the total weight of the cream.

Emulsifiers such as nonionic surface active agents, e.g., polysorbate 60 (available from ICI Americas), sorbitan monostearate, polyglyceryl-4 oleate, and polyoxyethylene(4) lauryl ether or trivalent cationic a cream of the invention. A cream can contain one or more emulsifiers. Generally the total amount of emulsifier is preferably about 2 percent to about 14 percent, and more preferably about 2 percent to about 6 percent by weight based on the total weight of the cream.

Pharmaceutically acceptable thickeners, such as Veegum™K (available from R. T. Vanderbilt Company, Inc.), and long chain alcohols (i.e. cetyl alcohol, stearyl alcohol or cetearyl alcohol) can be used. A cream can contain one or more thickeners. The total amount of thickener present is preferably about 3 percent to about 12 percent by weight based on the total weight of the cream.

Preservatives such as methylparaben, propylparaben and benzyl alcohol can be present in a cream of the invention. The appropriate amount of such preservative(s) is known to those skilled in the art.

Optionally, an additional solubilizing agent such as benzyl alcohol, lactic acid, acetic acid, stearic acid or hydrochloric acid can be included in a cream of the invention.

If an additional solubilizing agent is used, the amount present is preferably about 1 percent to about 12 percent by weight based on the total weight of the cream.

Optionally, a cream of the invention can contain a humectant such as glycerin, skin penetration enhancers such as butyl stearate, and additional solubilizing agents.

It is known to those skilled in the art that a single ingredient can perform more than one function in a cream, i.e., cetyl alcohol can serve both as an emollient and as a thickener.

Generally, a cream consists of an oil phase and a water phase mixed together to form an emulsion. Preferably, the amount of water present in a cream of the invention is about 45 percent to about 85 percent by weight based on the total weight of the cream.

The oil phase of a cream of the invention can be prepared by first combining the 1-isobutyl-1H-imidazo[4,5-c]quinolin-4-amine and the fatty acid (if the cream contains benzyl alcohol it can also be added at this point) and heating with occasional stirring to a temperature of about 50° C. to 85° C. When the 1-isobutyl-1H-imidazo[4,5-c]quinolin-4-amine appears to be completely dissolved, the remaining oil phase ingredients are added and heating is continued until dissolution appears to be complete.

The water phase can be prepared by combining all other ingredients and heating with stirring until dissolution appears to be complete.

The creams of the invention are generally prepared by adding the water phase to the oil phase with both phases at a temperature of about 65° C. to 75° C. The resulting emulsion is mixed with a suitable mixer apparatus to give the desired cream.

An ointment of the invention contains an ointment base in addition to 1-isobutyl-1H-imidazo[4,5-c]quinolin-4-amine and fatty acid.

The amount of 1-isobutyl-1H-imidazo[4,5-c]-quinolin-4-amine present in an ointment of the invention is preferably about 0.5 percent to about 9 percent, and more preferably about 0.5 percent to about 5 percent by weight based on the total weight of the ointment.

The total amount of fatty acid present in an ointment of the invention is preferably about 3 percent to about 45 percent, and more preferably about 3 percent to about 25 percent based on the total weight of the ointment.

A pharmaceutically acceptable ointment base such as petrolatum or polyethylene glycol 400 (available from Union Carbide) in combination with polyethylene glycol 3350 (available from Union Carbide) can be used. The amount of ointment base present in an ointment of the invention is preferably about 60 percent to about 95 percent by weight based on the total weight of ointment.

Optionally, an ointment of the invention can also contain emollients, emulsifiers and thickeners. The emollients, emulsifiers, and thickeners and the preferred amounts thereof described above in connection with creams are also generally suitable for use in an ointment of the invention.

An ointment according to the invention can be prepared by combining 1-isobutyl-1H-imidazo[4,5-c]quinolin-4-amine with fatty acid and heating with occasional stirring to a temperature of about 65° C. When the 1-isobutyl-1H-imidazo[4,5-c]-quinolin-4-amine appears to be completely dissolved, the remaining ingredients are added and heated to about 65° C. The resulting mixture is mixed with a suitable mixer while being allowed to cool to room temperature.

A pressure-sensitive adhesive composition of the invention contains 1-isobutyl-1H-imidazo[4,5-c]-quinolin-4-amine, fatty acid, and a pressure sensitive adhesive polymer.

The amount of 1-isobutyl-1H-imidazo[4,5-c]-quinolin-4-amine present in a pressure sensitive adhesive composition of the invention is preferably about 0.5 percent to about 9 percent by weight, and more preferably about 3 percent to about 7 percent by weight based on the total weight of the adhesive composition. The amount of fatty acid present is preferably about 10 percent to about 40 percent by weight, more preferably about 15 percent to about 30 percent by weight, and most preferably about 20 percent to about 30 percent by weight, based on the total weight of the adhesive composition.

Preferably, the adhesive polymer utilized in a pressure sensitive adhesive composition of the invention is substantially chemically inert to 1-isobutyl-1H-imidazo[4,5-c]quinolin-4-amine. The adhesive polymer is preferably present in an amount of about 55 percent to about 85 percent by weight based on the total weight of the composition. Suitable adhesive polymers include acrylic adhesives that contain, as a major constituent (i.e., at least about 80 percent by weight of all monomers in the polymer), a hydrophobic monomeric acrylic or methacrylic acid ester of an alkyl alcohol, the alkyl alcohol containing 4 to 10 carbon atoms. Examples of suitable monomers are those discussed below in connection with the "A Monomer". These adhesive polymers can further contain minor amounts of other monomers such as the "B Monomers" listed below.

Preferred adhesives include acrylic pressure-sensitive adhesive copolymers containing A and B Monomers as follows: Monomer A is a hydrophobic monomeric acrylic or methacrylic acid ester of an alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A Monomers are n-butyl, n-pentyl, n-hexyl, isoheptyl, n-nonyl, n-decyl, isohexyl, 2-ethyloctyl, isooctyl and 2-ethylhexyl acrylates. The most preferred A Monomer is isooctyl acrylate.

Monomer B is a reinforcing monomer selected from the group consisting of acrylic acid; methacrylic acid; alkyl acrylates and methacrylates containing 1 to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; n-vinyl-2-pyrrolidone; vinyl ethers such as vinyl tertiary-butyl ether; substituted ethylenes such as derivatives of maleic anhydride, dimethyl itaconate and monoethyl formate and vinyl perfluoro-n-butyrate. The preferred B Monomers are acrylic acid, methacrylic acid, the above-described alkyl acrylates and methacrylates, acrylamide, methacrylamide, and the above-described lower alkyl substituted acrylamides. The most preferred B Monomer is acrylamide.

In one embodiment of a pressure-sensitive adhesive composition of the invention, the pressure-sensitive adhesive copolymer containing A and B Monomers as set forth above preferably contains the A Monomer in an amount by weight of about 80 percent to about 98 percent of the total weight of all monomers in the copolymer. The A Monomer is more preferably present in an amount by weight of about 88 percent to about 98 percent, and is most preferably present in an amount by weight of about 91 percent to about 98 percent. The B Monomer in such a copolymer is preferably present in the pressure-sensitive adhesive copolymer in an amount by weight of about 2 percent to about 20 percent, more preferably about 2 percent to about 12 percent, and most preferably 2 to 9 percent of the total weight of the monomers in the copolymer.

In another embodiment of a pressure-sensitive adhesive composition of the invention, the adhesive copolymer comprises about 60 to about 80 percent by weight (and preferably about 70 to about 80 percent by weight) of the above-mentioned hydrophobic monomeric acrylic or methacrylic acid ester of an alkyl alcohol (i.e., Monomer A described above) based on the total weight of all monomers in the copolymer; about 4 to about 9 percent by weight based on the total weight of all monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide and N-vinyl-2-pyrrolidone; and about 15 to about 35 percent by weight (and preferably about 15 to about 25 percent by weight) of vinyl acetate based on the total weight of all monomers in the copolymer. In this embodiment the preferred acrylic or methacrylic acid ester is isooctyl acrylate and the preferred reinforcing monomer is acrylamide.

The above described adhesive copolymers are known, and methods of preparation therefor are well known to those skilled in the art, having been described for example, in U.S. Pat. No. 24,906 (Ulrich), the disclosure of which is incorporated herein by reference. The polymerization reaction can be carried out using a free radical initiator such as an organic peroxide (e.g., benzoylperoxide) or an organic azo compound (e.g., 2,2'-azobis(2,4-dimethylpentanenitrile), available under the trade designation "Vazo 52" from DuPont).

Since pressure-sensitive adhesives such as those described above are inherently rubbery and tacky and are suitably heat and light stable, there is no need to add tackifiers or stabilizers. However, such can be added if desired.

Optionally, a pressure sensitive adhesive composition of the invention can also contain one or more skin penetration enhancers such as glyceryl monolaurate, ethyl oleate, isopropyl myristate, diisopropyl adipate and N,N-dimethyldodecylamine-N-oxide, either as a single ingredient or as a combination of two or more ingredients. The skin penetration enhancer(s) preferably form a substantially homogeneous mixture with the pressure sensitive adhesive polymer or copolymer. The total amount of skin penetration enhancer(s) present in a pressure sensitive adhesive composition of the invention is preferably about 3 percent to about 25 percent by weight, more preferably about 3 percent to about 10 percent by weight based on the total weight of the adhesive composition.

When the skin penetration enhancer is a single ingredient, it is preferably a skin penetration enhancer such as isopropyl myristate, diisopropyl adipate, ethyl oleate, or glyceryl monolaurate.

When a combination skin penetration enhancer is used, it is preferably a combination such as: ethyl oleate with glyceryl monolaurate; ethyl oleate with N,N-dimethyldodecylamine-N-oxide; glyceryl monolaurate with N,N-dimethyldodecylamine-N-oxide; and ethyl oleate with both glyceryl monolaurate and N,N-dimethyldodecylamine-N-oxide.

A pressure-sensitive adhesive composition of the invention can be prepared by combining dry adhesive, 1-isobutyl-1H-imidazo[4,5-c]quinolin-4-amine, fatty acid, and skin penetration enhancer(s) with an organic solvent. The preferred organic solvents are methanol and ethyl acetate. The total solids content of the adhesive coating is preferably in the range of about 15 percent to about 40 percent, and more preferably in the range of about 20 to about 35 percent based on the total weight of the adhesive coating. The resulting mixture is shaken or mixed for a period of about 20 to 72 hours. When this method is used it is preferred that the 1-isobutyl-1H-imidazo[4,5-c]-quinolin-4-amine be in micronized form (i.e., particle size of 1-2 microns in diameter). Optionally, the mixture can be heated during shaking.

In a preferred method, the 1-isobutyl-1H-imidazo-4,5-c] quinolin-4-amine is combined with the fatty acid and shaken at 40° C. until there appears to be complete dissolution. The remaining ingredients are added and the mixture is shaken for a period of about 20 to 72 hours.

The pressure-sensitive adhesive compositions described above are preferably coated onto one surface of a suitable backing of sheet material, such as a film, to form a pressure-sensitive adhesive coated sheet material. A pressure-sensitive adhesive coated sheet material of the invention can be prepared by knife coating a suitable release liner to a predetermined uniform thickness with a wet adhesive formulation. This adhesive coated release liner is then dried and laminated onto a backing using conventional methods. Suitable release liners include conventional release liners comprising a known sheet material, such as a polyester web, a polyethylene web, or a polystyrene web, or polyethylene-coated paper, coated with a suitable silicone-type coating such as that available under the trade designation Daubert 164Z, from Daubert Co. The backing can be occlusive, non-occlusive or a breathable film as desired. The backing can be any of the conventional materials for pressure-sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the adhesive coating. The presently preferred backing is low density polyethylene.

The pressure-sensitive adhesive coated sheet material of the invention can be made in the form of an article such as a tape, a patch, a sheet, a dressing or any other form known to those skilled in the art.

Preferably, an article in the form of a patch is made from an adhesive coated sheet material of the invention and applied to the skin of a mammal. The patch is replaced as necessary with a fresh patch to maintain the particular desired therapeutic effect of the 1-isobutyl-1H-imidazo[4,5-c]quinolin-4-amine.

Inherent Viscosity Measurement

The inherent viscosity values reported in the Examples below were obtained by the conventional method used by those skilled in the art. The measurement of the viscosity of dilute solutions of the adhesive, when compared to controls run under the same conditions, clearly demonstrates the relative molecular weights. It is the comparative values that are significant; absolute figures are not required. In the examples, the inherent viscosity values were obtained using a Cannon-Fenske #50 viscometer to measure the flow time of 10 ml of a polymer solution (0.2 g polymer/deciliter tetrahydrofuran, in a water bath controlled at 25° C.). The examples and the controls were run under identical conditions. The test procedure followed and the apparatus used are explained in detail in the Textbook of Polymer Science, F. W. Billmeyer, Wiley-Interscience, 2nd Edition, 1971 under: Polymer chains and their characterization, D. Solution Viscosity and Molecular Size, pp 84-85, the disclosure and textbook of which is incorporated by reference.

The following examples are provided to illustrate the invention, but are not intended to be limiting thereof. Parts and percentages are by weight unless otherwise specified. Examples of creams, ointments and pressure sensitive adhesive compositions contemplated by the present invention are described in U.S. Pat. No. 4,689,338 and U.S. Pat. No. 5,238,944, which are incorporated herein by reference in their entireties. Percent modifications for, e.g., imiquimod and vehicle, to generate imiquimod formulations as described herein are likewise contemplated by the present invention. In addition, the formulations described and disclosed in U.S. patent application Ser. No. 11/276,324, are also contemplated by the present invention. Thus, U.S. patent application Ser. No. 11/276,324, is incorporated herein by reference in its entirety.

Preparative Method 1

Laboratory Scale Preparation of Isooctylacrylate/Acrylamide Copolymer

To a 114 gram narrow-mouth glass bottle were added: 18.6 g isooctyl acrylate, 1.4 g acrylamide, 0.04 g benzoyl peroxide, 27.0 g ethyl acetate and 3.0 g methanol. The solution was purged for thirty five seconds with nitrogen at a flow rate of one liter per minute. The bottle was sealed and placed in a rotating water bath at 55° C. for twenty-four hours to effect essentially complete polymerization. The polymer was diluted with ethyl acetate/methanol (90/10) to 23.2 percent solids and had a measured inherent viscosity of 1.26 dl/g in ethyl acetate.

Preparative Method 2

Pilot Plant Scale Preparation of Isooctylacrylate/Acrylamide Copolymer 155 kg isooctylacrylate, 11.6 kg acrylamide, 209.1 kg ethyl acetate and 23.2 kg methanol were charged to a clean, dry reactor. Medium agitation was applied. The batch was deoxygenated with nitrogen while heating to an induction temperature of 55° C. 114 g Lucidol™70 initiator (available from Pennwalt Corp.) mixed with 2.3 kg ethyl acetate was charged to the reactor. The temperature was maintained at 55° C. throughout the reaction. After 5.5 hours reaction time, 114 g Lucidol™70 mixed with 2.3 kg ethyl acetate were charged to the reactor. After 9.0 hours reaction time, an additional 114 g Lucidol™70 initiator mixed with 2.3 kg ethyl acetate were charged to the reactor. The reaction was continued until the percent conversion was greater than 98 percent as measured by gas chromatographic evaluation of residual monomer concentration. The resulting polymer solution was diluted to 25-28 percent solids with ethyl acetate/methanol (90/10) and had a measured Brookfield viscosity of 17,000-21,000 centipoises using spindle #4 at 12 rpm. The polymer had a measured inherent viscosity of 1.3-1.4 dl/g in ethyl acetate.

The above procedure was found to provide a pressure-sensitive adhesive that is equivalent in the practice of the present invention to a pressure-sensitive adhesive prepared according to PREPARATIVE METHOD 1.

A 25-30 percent solids solution of the isooctyl acrylate:acrylamide (93:7) adhesive copolymer in ethyl acetate/methanol (90:10) was coated onto a two-sided release liner using a knife-coater and coating at 0.5 mm in thickness. The adhesive-coated laminate was dried first at 82° C. for 3 minutes and then at 116° C. for 3 minutes. The dried adhesive coating was then stripped off the release liner and placed in a glass bottle. The foregoing procedure results in a reduction of the amount of any residual monomer in the adhesive copolymer.

Preparative Method 3

Preparation of Isooctyl Acrylate: Acrylamide: Vinyl Acetate (75:5:20) Copolymer

The procedure of PREPARATIVE METHOD 1 above acrylate, 8.0 g acrylamide, 32.0 g vinyl acetate, 0.32 g benzoyl peroxide, 216.0 g ethyl acetate and 24.0 g methyl alcohol. The resulting polymer was diluted with the ethyl acetate/methyl alcohol mixture to 21.52% solids. The adhesive polymer had a measured inherent viscosity of 1.40 dl/g in ethyl acetate at a concentration of 0.15 g/dl. Its Brookfield viscosity was 2,300 centipoise.

Preparative Method 4

Preparation of Isooctyl Acrylate Acrylamide: Vinyl Acetate (75:5:20) Copolymer

A master batch was prepared by combining 621.0 g of isooctyl acrylate, 41.4 g of acrylamide, 165.6 g of vinyl acetate, 1.656 g of 2,2'-azobis(2,4-dimethylpentanenitrile) (available from the DuPont Company as Vazo™52), 884.52 g of ethyl acetate and 87.48 g of methanol. A 400 g portion of the resulting solution was placed in an amber quart bottle. The bottle was purged for two minutes with nitrogen at a flow rate of one liter per minute. The bottle was sealed and placed in a rotating water bath at 45° C. for twenty-four hours to effect essentially complete polymerization. The copolymer was diluted with 250 g of ethyl acetate/methanol (90/10) to 26.05% solids and had a measured inherent viscosity of 1.27 dl/g in ethyl acetate at a concentration of 0.15 g/dl. Its Brookfield viscosity was 5580 centipoise.

EXAMPLE 1

A cream according to the present invention is prepared from the following ingredients:

| | % by Weight | Amount |
|---|---|---|
| Oil Phase | | |
| 1-Isobutyl-1H-imidazo[4,5-c]-quinolin-4-amine | 1.0 | 40.0 g |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase | | |
| Glycerin | 2.0 | 80.0 g |
| Methylparaben | 0.2 | 8.0 g |
| Propylparaben | 0.02 | 0.8 g |
| Purified water | 76.48 | 3059.2 g |

The materials listed above were combined according to the following procedure:

The glycerin, methylparaben, propylparaben and water were weighed into a 4 liter glass beaker then heated on a hot plate with stirring until the parabens isostearic acid and 1-isobutyl-1H-imidazo[4,5-c]-quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°-75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

EXAMPLES 2-9

Using the general method of Example 1, the cream formulations shown in Tables 1 and 2 are prepared.

TABLE 1

| | % by Weight Example | | | |
|---|---|---|---|---|
| | 2 | 3 | 4 | 5 |
| Oil Phase | | | | |
| 1-Isobutyl-1H-imidazo-[4,5-e]quinolin-4-amine | 1.0 | 1.0 | 1.0 | 1.0 |
| Isostearic acid | 10.0 | 10.0 | 5.0 | 5.0 |
| Benzyl alcohol | | 2.0 | | |
| Cetyl alcohol | | 1.7 | | |
| Stearyl alcohol | | 2.3 | | |
| Cetearyl alcohol | 6.0 | — | 6.0 | 6.0 |
| Polysorbate 60 | 2.55 | 2.55 | 2.55 | 2.55 |
| Sorbitan monostearate | 0.45 | 0.45 | 0.45 | 0.45 |
| Brij .TM. 30$^a$ | | | | 10.0 |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 77.78 | 77.78 | 82.78 | 72.78 |

Brij .TM. 30 (polyoxyethylene(4) lauryl ether) is available from ICI Americas, Inc.

TABLE 2

|  | % by Weight Example | | | |
|---|---|---|---|---|
|  | 6 | 7 | 8 | 9 |
| Oil Phase | | | | |
| 1-Isobutyl-1H-imidazo-r4,5-c]quinolin-4-amine | 1.0 | 1.0 | 1.0 | 1.0 |
| Isostearic acid | 10.0 | 25.0 | 10.0 | 6.0 |
| Benzyl alcohol |  | 2.0 |  | 2.0 |
| Cetyl alcohol |  | 2.2 | 1.7 |  |
| Stearyl alcohol |  | 3.1 | 2.3 |  |
| Cetearyl alcohol | 6.0 | — |  | 6.0 |
| Polysorbate 60 | 2.55 | 3.4 | 2.55 | 2.55 |
| Sorbitan monostearate | 0.45 | 0.6 | 0.45 | 0.45 |
| Brij .TM. 30 | 10.0 | — |  |  |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

EXAMPLE 10

A cream according to the present invention is prepared from the following ingredients:

|  | % by Weight | Amount |
|---|---|---|
| Oil Phase | | |
| 1-Isobutyl-1H-imidazo[4,5-4-quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |
| Aluminum stearate | 8.0 | 24.0 g |
| Cetyl alcohol | 4.0 | 12.0 g |
| Witconol .TM. 14$^a$ | 3.0 | 9.00 g |
| Acetylated lanolin | 1.0 | 3.0 g |
| Propylparaben | 0.063 | 0.19 g |
| Aqueous Phase | | |
| Veegum .TM. K$^b$ | 1.0 | 3.0 g |
| Methylparaben | 0.12 | 0.36 g |
| Purified water | 49.017 | 147.05 g |

$^a$Witconol .TM. 14 (polyglyceryl4 oleate) is available from Witco Chemical Corp. Organics Division
$^b$Veegum .TM. K (colloidal magnesium aluminum silicate) is available from R. T. Vanderbilt Company Inc.

The materials listed above were combined according to the following procedure:

The 1-isobutyl-1H-imidazo[4,5-c]quinolin-4-amine and the isostearic acid were weighed into a glass jar and heated with occasional stirring until the amine was dissolved (the temperature reached 68° C.). To this solution was added, the petrolatum, mineral oil, aluminum stearate, cetyl alcohol, Witconol™14, acetylated lanoline and propylparaben. The mixture was heated to 75° C. In a separate beaker, the methylparaben and water were combined and heated until the paraben dissolved (the temperature reached 61° C.). The Veegum™K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

EXAMPLE 11

An ointment according to the present invention is prepared from the following ingredients:

|  | % by Weight | Amount |
|---|---|---|
| 1-Isobutyl-1H-imidazo[4,5-c]quinolin-4-amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| Witconol .TM. 14 | 3.0 | 0.60 g |
| Aluminum stearate | 8.0 | 1.60 g |

The materials listed above are combined according to following procedure:

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

EXAMPLE 12

Using the general procedure of Example 11 an ointment containing the following ingredients is prepared.

|  | % by Weight | Amount |
|---|---|---|
| 1-Tsobutyl-1H-imidazo[4,5-c]-quinolin-4-amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

EXAMPLES 13-15

Creams of the present invention are prepared using the ingredients shown in Table 3. The Example 1 except that benzyl alcohol was used with the isostearic acid to dissolve the 1-isobutyl-1H-imidazo[4,5-c]quinolin-4-amine.

TABLE 3

|  | Example | | |
|---|---|---|---|
|  | 13 | 14 | 15 |
|  | % by Weight | | |
| Oil Phase | | | |
| 1-Isobutyl-1H-imidazo[4,5-4-quinolin-4-amine | 5.0 | 5.0 | 4.85 |
| Isostearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum |  |  | 2.91 |
| Polysorbate 60 | 3.4 | 3.4 | 4.13 |
| Sorbitan monostearate | 0.6 | 0.6 | 0.73 |
| Stearic acid |  |  | 9.71 |

TABLE 3-continued

| | Example | | |
|---|---|---|---|
| | 13 | 14 | 15 |
| | % by Weight | | |
| Aqueous Phase | | | |
| Glycerin | 2.0 | 2.0 | 1.94 |
| Methylparaben | 0.2 | 0.2 | 0.19 |
| Propylparaben | 0.02 | 0.02 | 0.02 |
| Purified water | 53.48 | 56.48 | 46.39 |

EXAMPLE 16

A cream according to the present invention is prepared from the following ingredients:

| | % by Weight | Amount |
|---|---|---|
| Oil Phase | | |
| 1-Isobutyl-1H-imidazo[4,5-c]-quinolin-4-amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |
| Aqueous Phase | | |
| 1-Isobutyl-1H-imidazo [4,5-c]-quinolin-4-amine | 1.0 | 0.2 g |
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above are combined according to the following procedure:

The isostearic acid and 0.8 g of 1-isobutyl-1H-imidazo[4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

EXAMPLE 17

A mixture of 5.9415 g of the 93:7 isooctyl acrylate:acrylamide adhesive copolymer prepared in PREPARATIVE METHOD 2 above, 1.5126 g isostearic acid, 2.0075 g ethyl oleate, 0.3021 g glyceryl monolaurate, 0.2936 1-isobutyl-1H-imidazo[4,5-c]quinolin-4-amine (micronized) and 23.7 g of 90:10 ethyl acetate:methanol was placed in a small glass jar. The jar was placed on a horizontal shaker and shaken at room temperature for about 13 hours. The formulation was coated at a thickness of 20 mils onto a 5 mil Daubert 164Z liner. The laminate was oven dried for 3 minutes at 105° F., for 2 minutes at 185° F., and for 2 minutes at 210° F. The resulting adhesive coating contained 59.1 percent 93:7 isooctyl acrylate:acylamide adhesive copolymer, 15.0 percent isostearic acid, 20.0 percent ethyl oleate, 3.0 percent glyceryl monolaurate and 2.9 percent 1-isobutyl-1H-imidazo[4,5-c]quinolin-4-amine. The material was then laminated with 3 mil low density polyethylene backing and die cut into 2.056 cm.sup.2 patches.

EXAMPLES 18-20

Pressure-Sensitive Adhesive Coated Sheet Materials Prepared Using Unmicronized 1-Isobutyl-1H-imidazo[4,5-c]quinolin-4-amine Using the general method of Example 17 the formulations shown below are prepared, 1-Isobutyl-1H-imidazo[4,5-c] quinolin-4-amine that had been ground with a mortar and pestle was used. The adhesive was the 93:7 isooctyl acrylate: acrylamide copolymer prepared in PREPARATIVE METHOD 1 above. The solvent was 90:10 ethyl acetate: methanol. All formulations were mixed at room temperature.

| | Example | | |
|---|---|---|---|
| | 18 | 19 | 20 |
| 1-Isobutyl-1H-imidazo[4,5-0-quinolin-4-amine Ethyl oleate | 5.0 5.1 | 3.0 5.0 | 3.0 8.0 |
| Isostearic acid | 10.0 | 10.0 | 6.0 |
| Oleic acid | 20.0 | 20.0 | 13.0 |
| Glyceryl monolaurate | 1.5 | 1.5 | 1.5 |
| N,N-dimethyldodecylamine-N-oxide Adhesive | 1.0 57.4 | 1.1 59.3 | 3.0 65.4 |

EXAMPLE 21

A formulation with the same components in the same proportions as Example 18 is prepared using a different method. The 1-isobutyl-1H-imidazo[4,5-c]-quinolin-4-amine was combined with the oleic and isostearic acids and shaken at 40° C. until there was complete dissolution of the 1-isobutyl-1H-imidazo-[4,5-c]quinolin-4-amine. The remaining ingredients were added and shaken a 40° C. for 72 hours. Patches measuring 2.056 cm.sup.2 were prepared by the general method of Example 17.

EXAMPLE 22

A mixture of 2.4734 g 1-isobutyl-1H-imidazo[4,5-c]-quinolin-4-amine 3.3315 g isostearic acid and 6.6763 g oleic acid is prepared. To 1.8738 g of the above mixture was added 2.8750 g of the 93:7 isooctyl acrylate:acryamide adhesive copolymer prepared in PREPARATIVE METHOD 2 above, 0.2548 g of ethyl oleate, 0.0510 g N,N-dimethyldodecylamine-N-oxide, 0.0820 g glyceryl monolaurate (from Lauricidin, Inc.) and 14.0457 g of 90:10 ethyl acetate/methanol. The above was shaken for 30 hours at room temperature on a horizontal shaker. Transdermal patches were then prepared generally according to the procedures of Example 17.

EXAMPLE 23

Creams are prepared in accordance with the present invention using the ingredients shown in this Example 23.

| Excipients | % w/w | % w/w | % w/w | % w/w | % w/w |
|---|---|---|---|---|---|
| Isostearic Acid | 10.00 | 12.50 | 25.00 | 10.00 | 15.00 |
| Cetyl alcohol | 2.20 | 2.20 | 2.70 | 4.00 | 4.00 |
| Stearyl alcohol | 3.10 | 3.10 | 3.80 | 2.00 | 2.00 |
| White petroleum | 5.00 | 5.00 | 3.00 | 3.40 | 2.80 |
| Polysorbate 60 | 3.40 | 3.40 | 3.40 | 3.80 | 3.00 |
| Sorbitan Monostearate | 0.60 | 0.60 | 0.60 | 1.00 | 1.00 |
| Glycerin | 5.00 | 5.00 | 2.00 | 1.00 | 3.00 |
| Xanthan gum | 0.50 | 0.50 | 0.50 | 0.30 | 0.70 |
| Purified water | 65.98 | 63.48 | 54.78 | 70.28 | 64.28 |
| Benzyl alcohol | 2.00 | 2.00 | 2.00 | 2.00 | 2.00 |
| Methylparaben | 0.20 | 0.20 | 0.20 | 0.20 | 0.20 |
| Propylparaben | 0.02 | 0.02 | 0.02 | 0.02 | 0.02 |
| Imiquimod | 2.00 | 2.00 | 2.00 | 2.00 | 2.00 |
| Total: | 100.00 | 100.00 | 100.00 | 100.00 | 100.00 |

EXAMPLE 24

Creams are prepared in accordance with the present invention using the ingredients shown in this Example 24.

| Excipients | % w/w | % w/w | % w/w | % w/w | % w/w |
|---|---|---|---|---|---|
| Isostearic Acid | 15.00 | 12.50 | 25.00 | 15.00 | 10.00 |
| Cetyl alcohol | 2.20 | 2.20 | 2.20 | 2.00 | 2.00 |
| Stearyl alcohol | 3.10 | 3.10 | 3.10 | 2.00 | 2.40 |
| White petroleum | 6.00 | 5.00 | 3.00 | 3.40 | 2.80 |
| Polysorbate 60 | 3.00 | 3.00 | 3.40 | 3.80 | 3.80 |
| Sorbitan Monostearate | 1.00 | 1.00 | 0.60 | 0.20 | 1.00 |
| Glycerin | 5.00 | 5.00 | 2.00 | 3.00 | 3.00 |
| Xanthan gum | 1.00 | 0.50 | 1.00 | 0.30 | 0.30 |
| Purified water | 60.23 | 63.23 | 55.23 | 66.83 | 70.23 |
| Benzyl alcohol | 1.00 | 2.00 | 2.00 | 1.00 | 2.00 |
| Methylparaben | 0.20 | 0.20 | 0.20 | 0.20 | 0.20 |
| Propylparaben | 0.02 | 0.02 | 0.02 | 0.02 | 0.02 |
| Imiquimod | 2.25 | 2.25 | 2.25 | 2.25 | 2.25 |
| Total: | 100.00 | 100.00 | 100.00 | 100.00 | 100.00 |

EXAMPLE 25

Creams are prepared in accordance with the present invention using the ingredients shown in this Example 25.

| Excipients | % w/w | % w/w | % w/w | % w/w | % w/w | % w/w |
|---|---|---|---|---|---|---|
| Isostearic Acid | 15.00 | 15.00 | 10.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petroleum | 15.50 | 3.00 | 8.50 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 52.98 | 65.48 | 61.98 | 60.48 | 59.23 | 59.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total: | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Isostearic Acid | 15.00 | 15.00 | 15.00 | 25.00 | 12.5 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petroleum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 65.48 | 59.48 | 59.48 | 55.48 | 62.98 | 54.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Isostearic Acid | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petroleum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.98 | 65.58 | 58.48 | 57.48 | 55.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

EXAMPLE 26

Creams are prepared in accordance with the present invention using the ingredients shown in this Example 26.

| Excipients | % w/w | % w/w | % w/w | % w/w | % w/w |
|---|---|---|---|---|---|
| Isostearic Acid | 15.00 | 18.00 | 15.00 | 20.00 | 12.50 |
| Cetyl alcohol | 2.00 | 2.00 | 2.00 | 2.00 | 2.20 |
| Stearyl alcohol | 2.00 | 2.00 | 2.40 | 2.40 | 3.10 |
| White petroleum | 3.40 | 2.80 | 3.40 | 2.80 | 5.00 |
| Polysorbate 60 | 3.00 | 3.80 | 3.00 | 3.00 | 3.40 |
| Sorbitan Monostearate | 1.00 | 1.00 | 0.20 | 0.20 | 0.60 |
| Glycerin | 3.00 | 2.00 | 1.00 | 3.00 | 6.00 |
| Xanthan gum | 0.30 | 0.70 | 0.70 | 0.30 | 0.50 |
| Purified water | 65.08 | 62.48 | 67.08 | 61.08 | 61.48 |
| Benzyl alcohol | 2.00 | 2.00 | 2.00 | 2.00 | 2.00 |
| Methylparaben | 0.20 | 0.20 | 0.20 | 0.20 | 0.20 |
| Propylparaben | 0.02 | 0.02 | 0.02 | 0.02 | 0.02 |
| Imiquimod | 3.00 | 3.00 | 3.00 | 3.00 | 3.00 |
| Total: | 100.00 | 100.00 | 100.00 | 100.00 | 100.00 |

EXAMPLE 27

Creams are prepared in accordance with the present invention using the ingredients shown in this Example 27.

| Excipients | % w/w | % w/w | % w/w | % w/w | % w/w |
|---|---|---|---|---|---|
| Isostearic Acid | 15.00 | 20.00 | 15.00 | 20.00 | 10.00 |
| Cetyl alcohol | 2.00 | 2.00 | 4.00 | 4.00 | 2.20 |
| Stearyl alcohol | 2.00 | 2.40 | 2.40 | 2.40 | 3.10 |
| White petroleum | 3.40 | 2.80 | 2.50 | 3.40 | 5.00 |
| Polysorbate 60 | 3.00 | 3.00 | 3.00 | 3.80 | 3.40 |
| Sorbitan Monostearate | 1.00 | 0.20 | 1.00 | 1.00 | 0.60 |
| Glycerin | 3.00 | 3.00 | 1.00 | 3.00 | 5.00 |
| Xanthan gum | 0.30 | 0.30 | 0.30 | 0.70 | 0.50 |
| Purified water | 64.83 | 60.83 | 65.33 | 57.23 | 64.73 |
| Benzyl alcohol | 2.00 | 2.00 | 2.00 | 1.00 | 2.00 |
| Methylparaben | 0.20 | 0.20 | 0.20 | 0.20 | 0.20 |
| Propylparaben | 0.02 | 0.02 | 0.02 | 0.02 | 0.02 |
| Imiquimod | 3.25 | 3.25 | 3.25 | 3.25 | 3.25 |
| Total: | 100.00 | 100.00 | 100.00 | 100.00 | 100.00 |

EXAMPLE 28

Creams are prepared in accordance with the present invention using the ingredients shown in this Example 28.

| Excipients | % w/w | % w/w | % w/w | % w/w | % w/w |
|---|---|---|---|---|---|
| Isostearic Acid | 15.00 | 10.00 | 12.50 | 19.00 | 20.00 |
| Cetyl alcohol | 2.00 | 2.20 | 2.20 | 2.20 | 2.20 |
| Stearyl alcohol | 2.40 | 3.10 | 3.10 | 3.10 | 3.10 |
| White petroleum | 3.40 | 5.00 | 5.00 | 3.00 | 3.00 |
| Polysorbate 60 | 3.00 | 3.40 | 4.00 | 3.40 | 3.40 |
| Sorbitan Monostearate | 0.20 | 0.60 | 0.60 | 0.60 | 0.60 |
| Glycerin | 1.00 | 4.00 | 5.00 | 2.00 | 6.00 |
| Xanthan gum | 0.70 | 0.50 | 0.50 | 0.50 | 0.50 |
| Purified water | 66.58 | 65.48 | 61.38 | 60.48 | 56.48 |
| Benzyl alcohol | 2.00 | 2.00 | 2.00 | 2.00 | 1.00 |
| Methylparaben | 0.20 | 0.20 | 0.20 | 0.20 | 0.20 |
| Propylparaben | 0.02 | 0.02 | 0.02 | 0.02 | 0.02 |
| Imiquimod | 3.50 | 3.50 | 3.50 | 3.50 | 3.50 |
| Total: | 100.00 | 100.00 | 100.00 | 100.00 | 100.00 |

EXAMPLE 29

Creams are prepared in accordance with the present invention using the ingredients shown in this Example 29.

| Excipients | % w/w | % w/w | % w/w | % w/w | % w/w | % w/w |
|---|---|---|---|---|---|---|
| Isostearic Acid | 20.00 | 20.00 | 25.00 | 18.75 | 20.00 | 21.25 |
| Cetyl alcohol | 4.00 | 2.20 | 2.20 | 2.20 | 2.20 | 2.20 |
| Stearyl alcohol | 2.40 | 3.10 | 3.10 | 3.10 | 3.10 | 3.10 |
| White petroleum | 3.40 | 3.00 | 3.00 | 5.00 | 5.00 | 3.75 |
| Polysorbate 60 | 3.80 | 3.40 | 3.40 | 3.00 | 3.40 | 3.40 |
| Sorbitan Monostearate | 1.00 | 0.60 | 0.60 | 1.00 | 0.60 | 0.60 |
| Glycerin | 3.00 | 2.00 | 2.00 | 5.00 | 5.00 | 5.00 |
| Xanthan gum | 0.70 | 0.50 | 0.50 | 0.50 | 0.50 | 0.50 |
| Purified water | 55.73 | 59.23 | 54.23 | 55.48 | 54.23 | 54.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total: | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Isostearic Acid | 20.00 | 20.00 | 20.00 | 25.00 | 18.75 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petroleum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 59.23 | 53.23 | 53.23 | 54.23 | 55.48 | 53.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Isostearic Acid | 25.00 | 20.00 | 20.00 | 20.00 | 20.00 | 21.00 |
| Cetyl alcohol | 2.20 | 4.00 | 2.20 | 2.20 | 2.20 | 2.20 |
| Stearyl alcohol | 3.10 | 2.40 | 3.10 | 3.10 | 3.10 | 3.10 |
| White petroleum | 3.00 | 3.40 | 5.00 | 3.00 | 5.00 | 5.00 |
| Polysorbate 60 | 3.40 | 3.80 | 3.40 | 3.40 | 3.40 | 3.40 |
| Sorbitan Monostearate | 0.60 | 1.00 | 0.60 | 0.60 | 0.60 | 0.60 |
| Glycerin | 2.00 | 3.00 | 2.00 | 5.00 | 5.00 | 5.00 |
| Xanthan gum | 1.00 | 0.70 | 0.50 | 0.50 | 0.50 | 0.50 |
| Purified water | 53.73 | 55.73 | 57.23 | 56.23 | 54.23 | 53.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

EXAMPLE 30

Creams are prepared in accordance with the present invention using the ingredients shown in this Example 30.

| Excipients | % w/w | % w/w | % w/w | % w/w | % w/w | % w/w |
|---|---|---|---|---|---|---|
| Isostearic Acid | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petroleum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

EXAMPLE 31

Creams are prepared in accordance with the present invention using the ingredients shown in this Example 31.

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 6.00 | 6.00 | 6.00 | 6.00 | 6.00 | 6.00 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | | 0.13 |
| Ammonium hydroxide solution | | | | | | 2.00 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 5.75 | 5.75 | 5.75 | 5.75 | 5.75 | 5.75 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | | 0.13 |
| Ammonium hydroxide solution | | | | | | 2.00 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 5.50 | 5.50 | 5.50 | 5.50 | 5.50 | 5.50 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | | 0.13 |
| Ammonium hydroxide solution | | | | | | 2.00 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 5.25 | 5.25 | 5.25 | 5.25 | 5.25 | 5.25 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | | 0.13 |
| Ammonium hydroxide solution | | | | | | 2.00 |
| Propylparaben | 0.02 | 0.02 | 0.02 | 0.02 | 0.02 | 0.02 |
| Imiquimod | 2.75 | 2.75 | 2.75 | 2.75 | 2.75 | 2.75 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |

-continued

| Excipients | % w/w | % w/w | % w/w | % w/w | % w/w | % w/w |
|---|---|---|---|---|---|---|
| White petroleum | 5.00 | 5.00 | 5.00 | 5.00 | 5.00 | 5.00 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 4.75 | 4.75 | 4.75 | 4.75 | 4.75 | 4.75 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 4.50 | 4.50 | 4.50 | 4.50 | 4.50 | 4.50 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 4.25 | 4.25 | 4.25 | 4.25 | 4.25 | 4.25 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 4.00 | 4.00 | 4.00 | 4.00 | 4.00 | 4.00 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

| Excipients | % w/w | % w/w | % w/w | % w/w | % w/w | % w/w |
|---|---|---|---|---|---|---|
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 3.75 | 3.75 | 3.75 | 3.75 | 3.75 | 3.75 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Oleic acid | 7.40 | 7.40 | 7.40 | | 7.40 | 7.40 |
| Stearic acid | 3.00 | 3.00 | 3.00 | | | |
| Linoleic acid | | | | 25.0 | | |
| Oleyl alcohol | | 10.0 | 10.0 | | | |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| Sorbitol 70% | | | | | 30.0 | |
| Castor oil | | | | | | 15.0 |
| Lactic acid | | | | | | 5.00 |
| Urea | | | | | | 5.00 |
| White petroleum | 3.50 | 3.50 | 3.50 | 3.50 | 3.50 | 3.50 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 2.00 | 2.00 | 2.00 |
| Xanthan gum | 0.50 | 0.50 | 0.50 | 0.50 | 0.50 | 0.50 |
| Purified water | 67.58 | 60.58 | 57.58 | 52.98 | 52.98 | 43.58 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Citric acid monohydrate | | | | | 0.13 | |
| Ammonium hydroxide solution | | | | | | 2.00 |
| Propylparaben | 0.02 | 0.02 | 0.02 | 0.02 | 0.02 | 0.02 |
| Imiquimod | 4.50 | 4.50 | 4.50 | 4.50 | 4.50 | 4.50 |
| Total | 100.00 | 100.00 | 100.00 | 100.00 | 100.00 | 100.00 |

It is believed that the creams of the present invention have Hydrophilic-lipophilic balance (HLB) values between about 12 and 15, and more preferably between about 12.4 and about 13.4.

What is claimed is:

1. A method for treating an external genital or perianal wart in a subject comprising:
    (a) applying a 3.75% w/w imiquimod composition to a dermatological area of the subject having the wart; and
    (b) allowing the imiquimod composition to remain in contact with the dermatological area for a sufficient time following the application whereby an effective amount of the imiquimod composition penetrates the dermatological area; and
   wherein the 3.75% w/w imiquimod composition is applied to the dermatological area of the subject once daily for up to 8 consecutive weeks or until clearance is observed, whichever occurs earlier, to treat the wart.

2. The method of claim 1, wherein imiquimod is the sole active pharmaceutical ingredient in the imiquimod composition applied to the dermatological area of the subject.

* * * * *